United States Patent [19]

Hagen et al.

[11] Patent Number: 4,845,226
[45] Date of Patent: Jul. 4, 1989

[54] PREPARATION OF 8-BROMOMETHYL-3-METHYLQUINOLINE COMPOUNDS

[75] Inventors: Helmut Hagen, Frankenthal; Rolf-Dieter Kohler, Edingen-Neckarhausen; Jacques Dupuis, Ludwigshafen, all of Fed. Rep. of Germany

[73] Assignee: BASF Aktiengesellschaft, Ludwigshafen, Fed. Rep. of Germany

[21] Appl. No.: 146,691

[22] Filed: Jan. 21, 1988

[30] Foreign Application Priority Data

Feb. 3, 1987 [DE] Fed. Rep. of Germany ....... 3703113

[51] Int. Cl.$^4$ .............................................. C07D 215/18
[52] U.S. Cl. .................... 546/180; 422/186; 546/170
[58] Field of Search ......................................... 546/180

[56] References Cited

PUBLICATIONS

Fuson, "Adv. Org. Chem.", Wiley, New York, N.Y., pp. 30–35, 288 and 289 (1950).
Chemical Abstract, vol. 199, No. 7, p. 167, 51427 (1984).

*Primary Examiner*—David B. Springer
*Attorney, Agent, or Firm*—Keil & Weinkauf

[57] ABSTRACT

A process for the preparation of 8-bromomethyl-3-methylquinoline compounds of the formula I

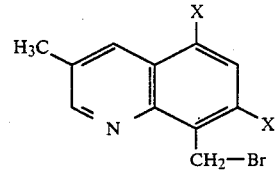

where one of both substituents X are chlorine and, where relevant, the other substituent X is hydrogen, by bromination of the corresponding 8-methylquinoline compound in the presence of a 2-phase mixture of a solvent stable to bromination and of, preferably, buffered water.

4 Claims, No Drawings

PREPARATION OF 8-BROMOMETHYL-3-METHYLQUINOLINE COMPOUNDS

The present invention realtes to the preparation of 8-bromomethyl-3-methylquinoline compounds of the formula (I)

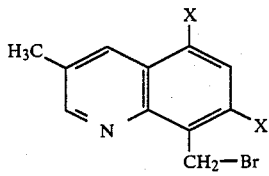

where one or both substituents X are chlorine and where the other substituent X, where relevant, is hydrogen. The compounds 1 can be used to prepare qunioline-8-carboxylic acids of the formula II

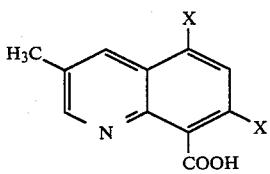

Quinolinecarboxylic acids are useful active ingredients in the crop protection sector.

In the past, it has been difficult to obtain bromomethyl compounds of the formula I in the required purity because the bromination of the corresponding 8-methylquinoline does not take place in a sufficiently selective manner.

It is an object of the present invention to provide the required bromomethyl compounds in high yield and purity.

We have found that this object is achieved, according to the invention, if the bromination of a corresponding 8-methylquinoline is carried out in a solvent which is stable to bromination and is immiscible, or not infinitely miscible, with water, and in the presence of water which is preferably buffered at weakly acidic pH.

Examples of suitable solvents are conventional ones, such as nitrobenzene or halohydrocarbons, eg. halobenzenes, chloroform or dichloroethane.

For example, an alkali metal acetate is added to the aqueous phase, the hydrogen bromide liberated producing a buffer effect at pH 4–5. Overall, the aqueous phase should essentially have a pH of 3–6 during the reaction.

The bromomethyl compound is obtained by brominating the corresponding methyl compound in the presence of a free radical initiator or in light at relatively low temperatures; depending on the type of free radical initiator or on the light wavelength, temperatures as low as from 0° to 20° C. are sufficient; commercial free radical initiators may require temperatures up to 100° C.

One of the commercial agents, such as azobisisobutyronitrile, is used as the free radical initiator, or exposure is effected using radiation of sufficiently short wavelength, as delivered, for example, by the discharge spectrum of a mercury vapor lamp.

The bromomethyl compound is in the nonaqueous phase after the reaction and can be extracted from this directly with aqueous sulfuric acid. In terms of process enginnering, the reaction can be coupled with the envisaged subsequent oxidation in a suitable manner, and the operating media, such as the halohydrocarbon and sulfuric acid, can be reused after suitable pretreatment.

The oxidation of the bromomethylquinoline compounds, which is necessary for obtaining quinoline carboxylic acid compounds, is advantageously carried out with nitric acid in the presence of sulfuric acid; we have found that this step of the process too can be improved. According to the invention, this step of the process too can be improved. According to the invention, the bromomethyl compound (I) is reacted with nitric acid by adding a heavy metal which, in moderately concentrated sulfuric acid containing nitric acid, forms polyvalent ions capable of existing in a plurality of valence states.

Compounds which provide heavy metals are, for example, halides and oxides of vanadium, chromium, molybdenum, tungsten, iron, cobalt, cerium, nickel, copper and certain platinum metals, eg. ruthenium and osmium. For simplicity, the oxides or halides can be added in elemental form, as can the metals. Manganese dioxide is particularly effective and is therefore preferred.

The reaction conditions are more advantageous than those of the known process. The reaction is carried out in general at from 50° to 100° C., ie. below the boiling point of the system, which is close to 140° C. under atmospheric pressure. A solution of the bromomethyl compound in about 50–80% strength sulfuric acid is initially taken, and moderately concentrated or concentrated nitric acid is used. In practice, for example, the following procedure is adopted: the bromomethyl compound in the sulfuric acid is initially taken at about 80°–100° C., and about 2.5–5 equivalents, based on 1 mole of the bromine compound, of nitric acid are then gradually added. The reaction takes place in the course of from 5 to 6 hours, or faster or slower, depending on the temperature.

The mixture is diluted with water and brought to pH 2.5–3.5 (all quinoline compounds, including any by-products, being precipitated) and the carboxylic acid is obtained, after extraction with methanol, isopropanol or the like in the form of a residue which can, if necessary, be purified by recrystallization.

The reaction can be carried out batchwise, for example in a stirred kettle, or continuously according to the conventional rules of process engineering, and stirred kettles with a downstream tube reactor, stirred kettle cascades or tube reactors can be used.

EXAMPLE 1

Preparation of 8-bromomethyl-7-chloro-3-methylquinoline 9.6 g of 7-chloro-3,8-dimethylquinoline are dissolved in 850 g of 1,2-dichlorobenzene, 6.2 g of sodium acetate, dissolved in 150 ml of water, and then 8 g of bromine are added, and the mixture is exposed to a 150 watt low pressure mercury lamp for from 5 to 6 hours at 15° C. The yield, determined chromatographically, is 80% of theory, based on converted dimethylquinoline. The selectivity of the reaction is 88% at a conversion of 91%. Table 1 sumarizes the result of varying the reaction conditions.

TABLE 1

Variation of the reaction conditions in the photochemical bromination of 9.6 g of 7-chloro-3,8-dimethylquinoline

| Solvent | | | Tempera- | | Conver- |
|---|---|---|---|---|---|
| Type | Amount [g] | Br$_2$ [g] | ture [°C.] | Yield* [%] | sion** [%] |
| Dichlorobenzene | 850 | 8 | 15 | 80 | 91 |
| Chlorobenzene | 720 | 8 | 15 | 79 | 90 |
| Nitrobenzene | 780 | 8 | 20 | 78 | 91 |
| Di-, tri- and tetrachloromethane | 650 each | 8 each | 20 | 80–76 | 90 |
| Trifluorotrichloroethane | 880 | 8 | 20 | 83** | 92 |
| Dichlorobenzene | 40 | 8 | 25 | 61 | 85 |
| Dichloromethane | 35 | 8 | 25–30 | 63 | 86 |
| Dichlorobenzene | 60 | 8 | 70 | 55 | 81 |
| Dichlorobenzene | 40 | 8 | 35 | 60 | 87 |
| Dichlorobenzene | 40 | 7.2 | 40 | 63 | 78 |
| Dichlorobenzene | 40 | 6.4 | 40 | 62 | 74 |
| Dichlorobenzene | 40 | 4 | 40 | 45 | 45 |

*Based on 7-chloro-3,8-dimethylquinoline used
**After a reaction time of 10 hours

EXAMPLE 2

9.6 g of 7-chloro-3,8-dimethylquinoline in 65 g of 1,2-dichlorobenzene are initially taken, and 6.2 g of sodium acetate, dissolved in 15 ml of water, are added. The mixture is heated to 90° C., after which a solution of 0.07 g of α, α-azoisobutyronitrile in 4 g of 1,2-dichlorobenzene and a solution of 8 g of bromine in 4 g of 1,2-dichlorbenzene are simultaneously added dropwise at this temperature in the course of 10 minutes, and the mixture is stirred for 1 hour. The yield is 63% (determined chromatographically) and the conversion 87%. Table 2 shows how the yield changes in the course of the reaction.

TABLE 2

| | | Yield as a function of conversion | |
|---|---|---|---|
| Conversion [%] | Bromine [equ.] | Yield [%], based on | |
| | | quinoline used | quinoline converted |
| 9 | 0.2 | 8 | 89 |
| 23 | 0.9 | 19 | 83 |
| 44 | 0.5 | 35 | 80 |
| 70 | 0.7 | 53 | 76 |
| 76 | 0.8 | 58 | 76 |
| 85 | 1.0 | 62 | 73 |
| 97 | 1.4 | 67 | 70 |

Preparation of 7-chloro-3-methylquinoline-8-carboxylic acid 270.5 g of 8-bromomethyl-7-chloro-3-methylquinoline are dissolved in 950 g of 70% strength sulfuric acid, the solution is heated to 90° C. and 4.5 g of manganese dioxide are added. Thereafter, 290 g of 65% strength nitric acid are added dropwise in the course of 5 hours. The mixture is left to stand for a further 2 hours, cooled and diluted to twice the volume with water.

The pH is brought to 3 with concentrated sodium hydroxide solution, and the precipitate is filtered off.

The moist filter cake is boiled up with the same amount of methanol or isopropyl alcohol, and the mixture is filtered at 40° C. The acid thus obtained has a purity of 95%, and the yield is 96%. Depending on purity requirements, reprecipitation may be carried out using dilute sodium hydroxide solution (purity: 98%; yield: 92%).

EXAMPLE 3

7-chloro-3-methylqunioline-8-carboxylic acid; overall process 191.5 g of 7-chloro-3,8-dimethylquinoline are dissolved in 1,300 g of 1,2-dichlorobenzene. 86.1 g of sodium acetate, dissolved in 200 ml of water, are added. The mixture is heated to 90° C. and, on the one hand, 1.4 g of α, αazoisobutyronitrile, dissolved in 80 g of 1,2dichlorobenzene, and, on the other hand, 112 g of bromine, dissolved in 80 g of 1,2-dichlorobenzene, are added dropwise at this temperature in the course of from 10 to 20 minutes. After 1 hour at 90° C., the aqueous phase is separated off and the nonaqueous phase is extracted at this temperature, once with 750 g of 70% strength sulfuric acid and once with 250 g of the said acid.

The extracts are combined, 4.5 g of manganese dioxide are added and the mixture is then heated to 90°–100° C. A solution fo 236 g of 55% strength nitric acid and 84 g of concentrated sulfuric acid is then added dropwise in the course of 6 hours. After 2 hours at 90° C., the mixture is cooled, diluted with 2,000 ml of water and brought to pH 3 with concentrated sodium hydroxide solution. The precipitate is boiled up twice with the same amount of methanol or isopropyl alcohol and filtered off at 60° C. The 7-chloro-3-methylquinoline-8-carboxylic acid obtained as a residue is isolated in a yield of 85%, based on the dimethyl compound converted, and in a purity of 96% (mp.: 239°–242° C.).

The product can be reprecipitated from dilute sodium hydroxide solution to give 98% pure acid (mp.: 243°–244° C.) in a yield of 82%. From the extract collected, it is possible to distill off methanol and recover 74 g of 7-chloro-3,8-dimethylquinoline.

We claim:

1. A process for the production of 8-bromomethyl-3-methylquinoline compounds of the formula I

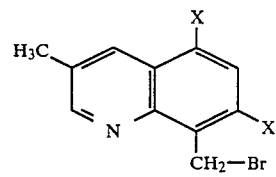

where the two radicals X denote chlorine or one of them denotes chlorine and the other hydrogen, which comprises reacting a corresponding 8-methylquinoline with bromine in a reaction medium consisting of an aqueous phase and a water-insoluble inert solvent as an organic phase.

2. A process as defined in claim 1, wherein the pH of the aqueous phase is kept at from 3 to 6.

3. A process as defined in claim 1, wherein the bromination is carried out with the additional aid of compounds forming free radicals.

4. A process as defined in claim 1, wherein the reaction is carried out at from 0° to 100° C.

* * * * *